United States Patent
Yuan et al.

(10) Patent No.: US 7,384,760 B2
(45) Date of Patent: Jun. 10, 2008

(54) METHODS FOR ASSAYING INHIBITORS OF S-ADENOSYLHOMOCYSTEINE (SAH) HYDROLASE AND S-ADENOSYLMETHIONINE (SAM)-DEPENDENT METHYLTRANSFERASE

(75) Inventors: Chong-Sheng Yuan, San Diego, CA (US); Qi-Zhuang Ye, San Diego, CA (US); Sheng-Xue Xie, Lawrence, KS (US)

(73) Assignee: General Atomics, San Diego, CA (US)

( * ) Notice: Subject to any disclaimer, the term of this patent is extended or adjusted under 35 U.S.C. 154(b) by 220 days.

(21) Appl. No.: 10/836,953

(22) Filed: Apr. 30, 2004

(65) Prior Publication Data

US 2005/0244912 A1 Nov. 3, 2005

(51) Int. Cl.
C12Q 1/48 (2006.01)
C12Q 1/34 (2006.01)
(52) U.S. Cl. .......................................... 435/15; 435/18
(58) Field of Classification Search ..................... None
See application file for complete search history.

(56) References Cited

U.S. PATENT DOCUMENTS

| | | | |
|---|---|---|---|
| 3,464,890 A | 9/1969 | Weichselbaum | |
| 3,647,070 A | 3/1972 | Adler | |
| 3,780,935 A | 12/1973 | Lucacs | |
| 3,843,443 A | 10/1974 | Fishman | |
| 3,852,194 A | 12/1974 | Zine et al. | |
| 3,939,123 A | 2/1976 | Matthews et al. | |
| 4,140,631 A | 2/1979 | Okuda et al. | |
| 4,162,355 A | 7/1979 | Tsibris | |
| 4,171,412 A | 10/1979 | Coupek | |
| 4,175,183 A | 11/1979 | Ayers | |
| 4,177,038 A | 12/1979 | Biebricher et al. | |
| 4,178,439 A | 12/1979 | Ayers et al. | |
| 4,179,402 A | 12/1979 | Kim et al. | |
| 4,180,524 A | 12/1979 | Reusser et al. | |
| 4,241,537 A | 12/1980 | Wood | |
| 4,244,721 A | 1/1981 | Gupta et al. | |
| 4,282,287 A | 8/1981 | Giese | |
| 4,439,585 A | 3/1984 | Gould et al. | |
| 4,477,575 A | 10/1984 | Vogel et al. | |
| 4,485,227 A | 11/1984 | Fox | |
| 4,542,102 A | 9/1985 | Dattagupta et al. | |
| 4,562,157 A | 12/1985 | Lowe et al. | |
| 4,569,789 A | 2/1986 | Blattler et al. | |
| 4,569,981 A | 2/1986 | Wenzel et al. | |
| 4,681,870 A | 7/1987 | Balint, Jr. et al. | |
| 4,762,881 A | 8/1988 | Kauer | |
| 4,795,699 A | 1/1989 | Tabor et al. | |
| 4,803,153 A | 2/1989 | Shibata et al. | |
| 4,885,250 A | 12/1989 | Eveleigh et al. | |
| 4,894,443 A | 1/1990 | Greenfield et al. | |
| 4,908,405 A | 3/1990 | Bayer et al. | |
| 4,952,394 A | 8/1990 | Senter | |
| 4,954,444 A | 9/1990 | Eveleigh et al. | |
| 5,137,877 A | 8/1992 | Kaneko et al. | |
| 5,292,814 A | 3/1994 | Bayer et al. | |
| 5,328,603 A | 7/1994 | Velander et al. | |
| 5,334,640 A | 8/1994 | Desai et al. | |
| 5,349,066 A | 9/1994 | Kaneko et al. | |
| 5,364,533 A | 11/1994 | Ogura et al. | |
| 5,416,193 A | 5/1995 | Desai | |
| 5,451,683 A | 9/1995 | Barrett et al. | |
| 5,612,474 A | 3/1997 | Patel | |
| 5,618,528 A | 4/1997 | Cooper et al. | |
| 5,679,548 A | 10/1997 | Barbas et al. | |
| 5,834,184 A | 11/1998 | Harada et al. | |
| 5,854,023 A | 12/1998 | Hillman et al. | ............ 435/69.1 |
| 5,858,675 A | 1/1999 | Hillman et al. | |
| 5,859,227 A | 1/1999 | Giordano et al. | |
| 5,876,996 A | 3/1999 | Bandman et al. | ............ 435/193 |
| 6,610,504 B1 | 8/2003 | Yuan | ........................... 435/15 |

FOREIGN PATENT DOCUMENTS

| | | |
|---|---|---|
| DE | 197 57 571 | 6/1999 |
| WO | WO-86/03840 | 7/1986 |
| WO | WO-88/08137 | 10/1988 |
| WO | WO-93/15220 | 8/1993 |
| WO | WO-98/20156 | 5/1998 |
| WO | WO 03/060478 | 7/2003 |

OTHER PUBLICATIONS

U.S. Appl. No. 10/043,787, filed Jan. 10, 2002.
U.S. Appl. No. 10/410,879, filed Apr. 9, 2003.
Adams and Blumenthal, Biochemistry 36(27):8284-8292 (1997).
Ahmad and Rao, Gene 142(1):67-71 (1994).
Bauer et al., J. Biol. Chem. 263(30):15619-15625 (1988).
Bergwerff et al., Biochimie 74(1):25-37 91992).
Blanche et al., J. Bacteriol. 173(15):4637-4645 (1991).
Bokar et al., J. Biol. Chem. 269:17697-17704 (1994).
Bollivar et al., J. Bacteriol. 176(17):5290-5296 (1994).
Broach et al., Nature 384:14-16 91996).
Burbaum et al., Curr. Opin. Chem. Biol. 1:72-78 (1997).
Casellas and Jeanteur, Biochem. Biophys. Acta 519(1):243-254 (1978).
Casellas and Jeanteur, Biochem. Biophys. Acta 519(1):255-268 (1978).
Checovich et al., Nature 375:254-256 (1995).
Cheng et al., Cell 74(2):299-307 (1993).
Coulter-Karis and Hershfield, Ann. Hum. Genet. 53(2):169-175 (1989).
Creedon et al., J. Biol. Chem. 269(23):16364-16370 (1994).

(Continued)

Primary Examiner—Christopher R. Tate
Assistant Examiner—Amanda P. Wood
(74) Attorney, Agent, or Firm—Morrison & Foerster LLP

(57) ABSTRACT

The present invention relates to methods for assaying inhibitors for S-adenosylhomocysteine (SAH) hydrolases and assaying inhibitors for S-adenosylmethionine (SAM)-dependent methyltransferases. The methods are amenable for use in high throughput formats. Kits for performing the methods are also provided.

9 Claims, 1 Drawing Sheet

OTHER PUBLICATIONS

De Mot et al., Gene 150(1):199-200 (1994).
Edwards and Dixon, Arch. Biochem. Biophys. 287(2):372-379 (1991).
Fernandes, Journal of Biomolecular Screening 2:1 (1997).
Finta et al., Gene 164(1):65-69 (1995).
Geelen et al., Mol. Microbiol. 17(2):387-397 (1995).
Gibson et al., FEBS Lett. 352(2):127-130 (1994).
Gloria et al., Cancer 78:2300-2306 (1996).
Goswarmi et al., J. Biol. Chem. 257:6867-6870 (1982).
Henderson et al., Mol. Biochem. Parasitol. 53(1-2):169-183 (1992).
Higman and Niles, J. Biol. Chem. 269(21):14982-14987 (1994).
Hinchigeri et al., FEBS Lett. 407(3):337-342 (1997).
Hu et al., Biochemistry 38(26):8323-8333 (1999).
Itoh et al., J. Chromatogr. B. 692(1):217-221 (1997).
James et al., J. Biol. Chem. 270(38):22344-22350 (1995).
Jameson et al., Methods Enzymol. 246:283-300 (1995).
Janssen and Nes, J. Biol. Chem. 267(36):25856-25863 (1992).
Janzen et al., Lab Robotics Automation:8:261-265 (1996).
Jolley, Journal of Biomolecular Screening 1:33-38 (1996).
Kagan and Clarke, Arch. Biochem. Biophys.310(2):417-427 (1994).
Kelm et al., Eur. J. Biochem. 251(3):874-884 (1998).
Khouri et al., Arch. Biochem. Biophys. 265(1):1-7 (1988).
Knogge and Weissenbock, Eur. J. Biochem. 140(1):113-8 (1984).
Kossykh et al., Nucleic Acids Res. 21(20):4659-4662 (1993).
Kramer et al., Cancer Res. 50:3838-3842 (1990).
Lauster et al., J. Mol. Biol. 206:313-321 (1989).
Leustek et al., J. Biol. Chem. 272(5):2744-2752 (1997).
Levine et al., Anal. Biochem. 247:83-88 (1997).
Lundblad et al., Mol. Endocrinol. 10:607-612 (1996).
Lynch et al., Anal. Biochem. 247:77-82 (1997).
Madyastha et al., J. Biol. Chem. 248(7):2497-2501 (1973).
Maxwell et al., Arch. Biochem. Biophys. 293(1):158-166 (1992).
Minarovits et al., Virology 200:661-667 (1994).
Mozier et al., J. Biol. Chem. 263(10):4527-4531 (1988).
Muth and Nash, Antimicrob. Agents Chemother. 8(3):321-327 (1975).
O'Gara et al., J. Mol. Biol. 287(2):201-209 (1999).
Pakusch et al., Arch. Biochem. Biophys. 271(2):488-494 (1989).
Pimenta et al., Plant Physiol. 118(2):431-438 (1998).
Poeydomenge et al., Plant Cell Physiol. 105(2):749-750 (1994).
Posfai et al., Nucleic Acids Res. 17:2421-2435 (1989).
Powell et al., J. Mol. Bio. 234(1):60-71 (1993).
Powell et al., Nucleic Acids Res. 23(6):967-974 (1995).
Refsum et al., Clin. Chem. 31:624-628 (1985).
Robin et al., J. Bacteriol. 173(15):4893-4896 (1991).
Ross et al., Arch. Biochem. Biophys. 367(1):9-16 (1999).
Sato et al., Eur. J. Biochem. 225(1):125-131 (1994).
Schade et al., Anal. Biochem. 243:1-7 (1996).
Schanche et al., Molecular Pharmacology, 26:553-558 (1984).
Segal and Eichler, Arch. Biochem. Biophys. 275(2):334-343 (1989).
Shi et al., J. Biol. Chem. 271(16):9384-9389 (1996).
Silverman et al., Curr. Opin. Chem. Biol. 2(3):397-403 (1998).
Sittampalam et al. Curr. Opin. Biol. 1(3):384-391 (1997).
Som and Friedman, J. Biol. Chem. 266(5):2937-2945 (1991).
Syed et al., Biochemistry 32(9):2242-2247 (1993).
Takata and Fujioka, Biochemistry 31(17):4369-4374 (1992).
Takeshita et al., Plant Cell Physiol. 36(1):29-36 (1995).
Thibaut et al., J. Bacteriol. 172(11):6245-6251 (1990).
Tucker and Bestor, Mutat. Res. 386:119-130 (1997).
Turner et al., Nat. Struct. Biol. 5(5):369-376 (1998).
Upmeier et al., Arch. Biochem. Biophys. 262(2):445-454 (1988).
Van Loon et al., Biochem. Pharmacol. 44(4):775-785 (1992).
Vilbois et al., Eur. J. Biochem. 222(2):377-386 (1994).
Votruba and Holy, Coll. Czech. Chem. Commun. 454:3039-3044 (1980).
Wang et al., Plant Physiol. 114(1):213-221 (1997).
Wang et al., Arch Biochem. Biophys. 349(1):153-160 (1998).
Wenzel and Guschlbauer, Nucleic Acids Res. 21(19):4604-4609 (1993).
Willis et al., Cell. Biophys. 15:97-111 (1989).
Wojciechowski et al., Biochem. J. 136(2):405-412 (1973).
Wolfe and Borchardt, Journal of Medicinal Chemistry 34:1521-1530 (1991).
Wu et al., J. Gen. Microbiol. 138:2101-2112 (1992).
Yin et al., Biomedical Chemistry: Applying Chemical Principles to the Understanding and Treatment of Disease (Ed. Torrence), Chapter 2, "Mechanism-based S-adenosyl-L-homocysteine hydrolase inhibitors in the search for broad-spectrum antiviral agents," John Wiley & Sons, Inc. (2000).
Yu, Can. J. Biochem. Cell Biol. 62(10):964-969 (1984).
Yuan et al., Adv. Antiviral Drug Des. vol. 2, pp. 41-88, De Clercq (ed)., JAI Press, Inc., London, UK (1996).
Zawad and Sulser, Eur. J. Pharmacol. 124(1-2):157-160 (1986).
Bastin et al., (1996) Mol. Biochem. Parasitology 77:235-239.
Batra et al., (1993) Mol. Immunol. 30:379-386.
Bendixen et al., (1994) Nucl. Acids Res. 22:1778-1779.
Benoist and Chambon, (1981) Nature 290:304-310.
Braunwalder et al., (1996) J. Biomol. Screening 1:23-26.
Brown et al., (1997) Curr. Opin. Biotechnol. 8:45-49.
Buchko et al., (1999) Biochim. Biophys. Res. Commun. 254(1):109-113.
Burd and Dreyfuss, (1994) Embo J. 13:1197.
Burd and Dreyfuss, (1994) Science 265:615-621.
Chen and Katz, (1998) Bio. Techniques 25(1):22-24.
Cordingley et al., (1990) J. Biol. Chem. 265-9062.
Cumber et al., (1992) Bioconjugate Chem. 3:397-401.
cwirla et al., (1990) PNAS USA 87:6378-6382.
Dewitt et al., (1993) PNAS USA 90:6909.
Fattom et al., (1992) Infection & Immun. 60:584-589.
Feng et al., (1998) Cur. Biol. 8:267-278.
Germino et al., (1984) PNAS USA 81:4692.
Geysen et al., (1984) PNAS USA 81:3998-4002.
Goldmcher et al., (1992) Bioconj. Chem. 3:104-107.
Gonzalez et al., (1995) Biophys. J. 69:1272-1280.
Grunstein and Hogness, (1975) PNAs USA 72:3961-3965.
Habig et al., (1974) J. Biol. Chem. 249:7130.
Hadd et al., (1997) Anal. Chem. 69:3407-3412.
Hazum et al., (1981) In Pept., Proc. Eur. Pept. Symp., 16th, Brunfeldt, K (Ed), pp. 105-110.
Hinderliter et al., (1998) Biochim. Biophys. Acta 1448(2):227-235.
Houghten et al., (1985) PNAS USA 81:5131-5135.
Hutchinson et al., (1978) J. Biol. Chem. 253-6551.
St. Johnston et al., (1992) PNAS USA 89:10979-10983.
Kane et al., (1996) Anal. Biochem. 233(2):197-204.
Kang et al., (1997) Virus Res. 49(2):147-154.
Klein et al., (1997) J. Biomol. Screening 2:41-49.
Kolodziej and Young, (1991) Methods Enzymol. 194:508-519'.
Kozak, (1991) J. Biol. Chem. 266:19867-19870.
Kramer et al., (1990) Cancer Res 50:3838-3842.
Kuo et al., (1981( J. Immunol. Methods 43(1):35-47.
Ladurner et al., (1997) J. Mol. Biol. 273:330-337.
Lam et al., (1991) Nature 354:82-84.
Lester et al., (1996) J. Biol. Chem. 271:9460-9465.
Lieberman et al., (1994) Genes & Dev. 8:995-1006.
Lowenadler et al., (1987) Gene 58:87.
Lucas et al., (1998) J. Immunol. 161(7):3776-3780.
Lue et al., (1987) PNAS USA 84:8839-8843.
Maeji et al., (1992) J. Immunol. Met. 146:83-90.
Maru et al., (1996) J. Biol. Chem. 271:15353.
Mathis, (1995) Clin. Chem. 41:1391-1397.
Maxam and Gilbert, (1980) Meth. Enzymol. 65:499-560.
Mc Tigue et al., (1995) J. Mol. Biol. 246:21.
Merrifield, (1964) Biochemistry 3:1385-1390.
Murre et al., (1989) Cell 56:777-783.
Nagai and Thogersen, (1987) Methods Enzymol. 153-461.
Nagelkerken et al., (1997) Electrophoresis 18:2684-2698.
Nielsen et el., (1983) ONAS USA 80:5198.
Nilsson et al., (1985) Embo J. 4:1075.
Nosaka et al., (2000) Cancer Res. 60:1043-1048.
Olah et al., (1994) Anal. Biochem. 221:94-102.
Post et al., (1999) Cardiovasc. Res. 43:985-991.
Powers et al., (1989) Biotechnol. Bioeng. 33:173.
Prickett et al., (1989) Bio. Techniques 7(6):580-584.
Pu et al., (1992) Nucl. Acids Res. 20:771-775.

Rogers, (1997) Drug Discov. Today 2:306.
Rudiger et al., (1997) Bio. Techniques 23(1):96-97.
Schroeder et al., (1996) J. Biomol. Screening 1:75-80.
Schullek et al., (1997) Anal. Biochem. 246:20-29.
Sengupta et al., (1996) PNAs USA 93:8496-8501.
Senter et al., (1985) Photochem. Photobiol. 42:231-237.
Shapira et al., (1983) Gene 25:71.
Shilo and Weinberg, (1981) PNAS USA 78:6789-6792.
Smith and Johnson, (1988) Gene 7:31-40.
Sterrer et al., (1997) J. Recept. Signal Transduct. Res. 17:511-520.
Strauss et al., (1981) Gene 13:75-87.
Taylor et al., (1985) Nucleic Acids Res. 13:8765-8785.
Tolbert and Lameh, (1998) J. Neurochem. 70:113-119.
Toye et al., (1990) Infect. Immunity 58:3909.
Tseng and Verma, (1996) Gene 169:287-288.
Tullius et al., (1987) Meth. Enzymol. 155:537-558.
Waggoner et al., (1996) Hum. Pathol. 27:494-502.
Wang et al., (1990) Tetrahedron Lett. 31:6493-6496.
Wang et al., (1996) Gene 169(1):53-58.
Wang et al., (1996) Genes & Dev. 10:3028-3040.
Watson et al., (1996) BioTechniques 21(2):255-259.
Wellhoner et al., (1991) J. Biol. Chem. 266:4309-4314.
Williams et al., Biochemistry (1998) 37:7096-7102.
Xie et al., (1998) Endocrinology 139(11):4563-4567.
Yamaguchi et al., (1998) Oral Microbiol. Immunol, 13(6):348-354.
Yamamoto et al., (1980) Cell 22:787-797.
Yen et al. (1989) Makromol. Chem. 190:69-82.
You et al., (1997) Chem. Biol. 4:969-975.
Yuan et al., (1993) J. Biol. Chem. 268:17030-17037.
Yuan et al., (1996) J. Biol. Chem. 271:28009-28016.
Zapp et al., (1989) Nature 342:714.
U.S. Appl. No. 09/546,013, filed on Apr. 10, 2000.
Restriction Requirement from U.S. Appl. No. 09/546,013, mailed Dec. 5, 2001.
Examiner Interview Summary Record from U.S. Appl. No. 09/546,013, mailed on Jan. 2, 2002.
Response to Restriction Requirement from U.S. Appl. No. 09/546,016, filed on Jan. 3, 2002.
Non-Final Office Action from U.S. Appl. No. 09/546,016, mailed on Apr. 23, 2002.
Amendment Under 37 C.F.R. § 1.11 from U.S. Appl. No. 09/546,016, filed on Aug. 23, 2002.
Final Office action from U.S. Appl. No. 09/546,016, mailed on Dec. 9, 2002.
Amendment and Response Under 37 C.F.R. § 1.116 from U.S. Appl. No. 09/546,016, filed on Mar. 10, 2003.
Notice of Allowance from U.S. Appl. No. 09/546,016, mailed on Apr. 17, 2003.
Request for Certificate of Correction Pursuant to 37 CFR 1.322 from U. S. Appl. No. 546,016, filed Aug. 16, 2007.

SEQUENCE LISTING

```
<160> NUMBER OF SEQ ID NOS: 5

<210> SEQ ID NO 1
<211> LENGTH: 432
<212> TYPE: PRT
<213> ORGANISM: Homo sapiens

<400> SEQUENCE: 1

Met Ser Asp Lys Leu Pro Tyr Lys Val Ala Asp Ile Gly Leu Ala Ala
1               5                   10                  15

Trp Gly Arg Lys Ala Leu Asp Ile Ala Glu Asn Glu Met Pro Gly Leu
            20                  25                  30

Met Arg Met Arg Glu Arg Tyr Ser Ala Ser Lys Pro Leu Lys Gly Ala
        35                  40                  45

Arg Ile Ala Gly Cys Leu His Met Thr Val Glu Thr Ala Val Leu Ile
    50                  55                  60

Glu Thr Leu Val Thr Leu Gly Ala Glu Val Gln Trp Ser Ser Cys Asn
65                  70                  75                  80

Ile Phe Ser Thr Gln Asn His Ala Ala Ala Ile Ala Lys Ala Gly
            85                  90                  95
```

Ile Pro Val Tyr Ala Trp Lys Gly Glu Thr Asp Glu Tyr Leu Trp
            100                 105                 110
Cys Ile Glu Gln Thr Leu Tyr Phe Lys Asp Gly Pro Leu Asn Met Ile
        115                 120                 125
Leu Asp Asp Gly Gly Asp Leu Thr Asn Leu Ile His Thr Lys Tyr Pro
    130                 135                 140
Gln Leu Leu Pro Gly Ile Arg Gly Ile Ser Glu Glu Thr Thr Thr Gly
145                 150                 155                 160
Val His Asn Leu Tyr Lys Met Met Ala Asn Gly Ile Leu Lys Val Pro
                165                 170                 175
Ala Ile Asn Val Asn Asp Ser Val Thr Lys Ser Lys Phe Asp Asn Leu
            180                 185                 190
Tyr Gly Cys Arg Glu Ser Leu Ile Asp Gly Ile Lys Arg Ala Thr Asp
        195                 200                 205
Val Met Ile Ala Gly Lys Val Ala Val Ala Gly Tyr Gly Asp Val
    210                 215                 220
Gly Lys Gly Cys Ala Gln Ala Leu Arg Gly Phe Gly Ala Arg Val Ile
225                 230                 235                 240
Ile Thr Glu Ile Asp Pro Ile Asn Ala Leu Gln Ala Ala Met Glu Gly
                245                 250                 255
Tyr Glu Val Thr Thr Met Asp Glu Ala Cys Gln Glu Gly Asn Ile Phe
            260                 265                 270
Val Thr Thr Thr Gly Cys Ile Asp Ile Ile Leu Gly Arg His Phe Glu
        275                 280                 285
Gln Met Lys Asp Asp Ala Ile Val Cys Asn Ile Gly His Phe Asp Val
    290                 295                 300
Glu Ile Asp Val Lys Trp Leu Asn Glu Asn Ala Val Glu Lys Val Asn
305                 310                 315                 320
Ile Lys Pro Gln Val Asp Arg Tyr Arg Leu Lys Asn Gly Arg Arg Ile
                325                 330                 335
Ile Leu Leu Ala Glu Gly Arg Leu Val Asn Leu Gly Cys Ala Met Gly
            340                 345                 350
His Pro Ser Phe Val Met Ser Asn Ser Phe Thr Asn Gln Val Met Ala
        355                 360                 365
Gln Ile Glu Leu Trp Thr His Pro Asp Lys Tyr Pro Val Gly Val His
    370                 375                 380
Phe Leu Pro Lys Lys Leu Asp Glu Ala Val Ala Glu Ala His Leu Gly
385                 390                 395                 400
Lys Leu Asn Val Lys Leu Thr Lys Leu Thr Glu Lys Gln Ala Gln Tyr
                405                 410                 415
Leu Gly Met Ser Cys Asp Gly Pro Phe Lys Pro Asp His Tyr Arg Tyr
            420                 425                 430

<210> SEQ ID NO 2
<211> LENGTH: 2211
<212> TYPE: DNA
<213> ORGANISM: Homo sapiens

<400> SEQUENCE: 2
ctgaggccca gccccttcg cccgtttcca tcacgagtgc cgccagcatg tctgacaaac      60
tgccctacaa agtcgccgac atcggcctgg ctgcctgggg acgcaaggcc ctggacattg     120
ctgagaacga gatgccgggc ctgatgcgta tgcgggagcg gtactcggcc tccaagccac     180
tgaagggcgc ccgcatcgct ggctgcctgc acatgaccgt ggagacggcc gtcctcattg     240

```
agaccctcgt caccctgggt gctgaggtgc agtggtccag ctgcaacatc ttctccaccc    300
agaaccatgc ggcggctgcc attgccaagg ctggcattcc ggtgtatgcc tggaagggcg    360
aaacggacga ggagtacctg tggtgcattg agcagaccct gtacttcaag gacgggcccc    420
tcaacatgat tctggacgac gggggcgacc tcaccaacct catccacacc aagtacccgc    480
agcttctgcc aggcatccga ggcatctctg aggagaccac gactgggtc cacaacctct     540
acaagatgat ggccaatggg atcctcaagg tgcctgccat caatgtcaat gactccgtca    600
ccaagagcaa gtttgacaac ctctatggct gccgggagtc cctcatagat ggcatcaagc    660
gggccacaga tgtgatgatt gccggcaagg tagcggtggt agcaggctat ggtgatgtgg    720
gcaagggctg tgcccaggcc ctgcgggggtt cggagcccg cgtcatcatc accgagattg    780
accccatcaa cgcactgcag gctgccatgg agggctatga ggtgaccacc atggatgagg    840
cctgtcagga gggcaacatc tttgtcacca ccacaggctg tattgacatc atccttggcc    900
ggtaggtgcc agatggggggg tcccggggag tgagggagga gggcagagtt gggacagctt   960
tctgtccctg acaatctccc acggtcttgg gctgcctgac aggcactttg agcagatgaa    1020
ggatgatgcc attgtgtgta acattggaca ctttgacgtg gagatcgatg tcaagtggct    1080
caacgagaac gccgtggaga aggtgaacat caagccgcag gtggaccggt atcggttgaa    1140
gaatgggcgc cgcatcatcc tgctggccga gggtcggctg gtcaacctgg ttgtgccat     1200
gggccacccc agcttcgtga tgagtaactc cttcaccaac caggtgatgg cgcagatcga    1260
gctgtggacc catccagaca agtaccccgt tgggttcat ttcctgccca gaagctgga     1320
tgaggcagtg gctgaagccc acctgggcaa gctgaatgtg aagttgacca agctaactga    1380
gaagcaagcc cagtacctgg gcatgtcctg tgatggcccc ttcaagccgg atcactaccg    1440
ctactgagag ccaggtctgc gtttcaccct ccagctgctg tccttgccca ggccccacct    1500
ctcctcccta agagctaatg gcaccaactt tgtgattggt tgtcagtgt cccccatcga     1560
ctctctgggg ctgatcactt agtttttggc ctctgctgca gccgtcatac tgttccaaat    1620
gtggcagcgg gaacagagta ccctcttcaa gccccggtca tgatggaggt cccagccaca    1680
gggaaccatg agctcagtgg tcttggaaca gctcactaag tcagtccttc cttagcctgg    1740
aagtcagtag tggagtcaca aagcccatgt gttttgccat ctaggccttc acctggtctg    1800
tggacttata cctgtgtgct tggtttacag gtccagtggt tcttcagccc atgacagatg    1860
agaaggggct atattgaagg gcaaagagga actgttgttt gaattttcct gagagcctgg    1920
cttagtgctg ggccttctct taaacctcat tacaatgagg ттagтacтттт tagtccctgt   1980
тттacaggggg ttagaataga ctgttaaggg gcaactgaga aagaacagag aagtgacagc   2040
taggggttga gagggccag aaaaacatga atgcaggcag atttcgtgaa atctgccacc    2100
actttataac cagatggttc ctttcacaac cctgggtcaa aaagagaata atttggccta    2160
taatgttaaa agaaagcagg aaggtgggta aataaaaatc ttggtgcctg g             2211
```

<210> SEQ ID NO 3
<211> LENGTH: 9
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Val, Ile, or Leu
<220> FEATURE:
<221> NAME/KEY: VARIANT
<222> LOCATION: 2

```
<223> OTHER INFORMATION: Xaa = Leu or Val
<220> FEATURE:
<221> NAME/KEY: VARIANT
<222> LOCATION: 3
<223> OTHER INFORMATION: Xaa = Asp or Glu
<220> FEATURE:
<221> NAME/KEY: VARIANT
<222> LOCATION: 4
<223> OTHER INFORMATION: Xaa = Val or Ile
<220> FEATURE:
<221> NAME/KEY: VARIANT
<222> LOCATION: 6
<223> OTHER INFORMATION: Xaa = Gly or Cys
<220> FEATURE:
<221> NAME/KEY: VARIANT
<222> LOCATION: 8
<223> OTHER INFORMATION: Xaa = Thr or Pro

<400> SEQUENCE: 3

Xaa Xaa Xaa Xaa Gly Xaa Gly Xaa Gly
 1               5

<210> SEQ ID NO 4
<211> LENGTH: 8
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Pro or Gly
<220> FEATURE:
<221> NAME/KEY: VARIANT
<222> LOCATION: 2
<223> OTHER INFORMATION: Xaa = Gln or Thr
<220> FEATURE:
<221> NAME/KEY: VARIANT
<222> LOCATION: 3
<223> OTHER INFORMATION: Xaa = Phe, Tyr, or Ala
<220> FEATURE:
<221> NAME/KEY: VARIANT
<222> LOCATION: 6
<223> OTHER INFORMATION: Xaa = Ile, Val, or Tyr
<220> FEATURE:
<221> NAME/KEY: VARIANT
<222> LOCATION: 7
<223> OTHER INFORMATION: Xaa = Phe or Ile
<220> FEATURE:
<221> NAME/KEY: VARIANT
<222> LOCATION: 8
<223> OTHER INFORMATION: Xaa = Cys, Val, or Leu

<400> SEQUENCE: 4

Xaa Xaa Xaa Asp Ala Xaa Xaa Xaa
 1               5

<210> SEQ ID NO 5
<211> LENGTH: 10
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 7
<223> OTHER INFORMATION: Xaa = Arg, Ile, or Leu
<220> FEATURE:
<221> NAME/KEY: VARIANT
<222> LOCATION: 8
<223> OTHER INFORMATION: Xaa = Leu or Ile
<220> FEATURE:
<221> NAME/KEY: VARIANT
<222> LOCATION: 9
<223> OTHER INFORMATION: Xaa = Leu, Phe, Ile, or Val
```

```
-continued

<220> FEATURE:
<221> NAME/KEY: VARIANT
<222> LOCATION: 10
<223> OTHER INFORMATION: Xaa = Ile or Leu

<400> SEQUENCE: 5

Leu Leu Xaa Pro Gly Gly Xaa Xaa Xaa Xaa
1               5                   10
```

METHODS FOR ASSAYING INHIBITORS OF S-ADENOSYLHOMOCYSTEINE (SAH) HYDROLASE AND S-ADENOSYLMETHIONINE (SAM)-DEPENDENT METHYLTRANSFERASE

TECHNICAL FIELD

This invention relates generally to the field of assaying inhibitors of S-adenosylhomocysteine (SAH) hydrolase and assaying inhibitors of S-adenosylmethionine (SAM)-dependent methyltransferase.

BACKGROUND OF THE INVENTION

S-adenosylhomocysteine (SAH) hydrolase is a ubiquitous cellular enzyme catalyzing the hydrolysis of SAH to adenosine (Ado) and homocysteine (Hcy). SAH hydrolase has been an attractive therapeutic target for a number of medical indications including antiviral, anticancer, anti-inflammation, immunosuppression, and plasma Hcy-lowering for prevention or treatment of cardiovascular diseases due to its central role in regulation of biological methylation reactions. Yuan et al., *Exp. Opin. Ther. Patents*, 9: 1197-1206 (1999); Yuan et al., in *Adv. Antiviral Drug Des*. vol 2, pp. 41-88, De Clercq (ed)., JAI Press, Inc. London, UK (1996). Inhibition of SAH hydrolase results in inhibition of S-adenosyl-L-methionine (SAM)-dependent methylation reactions. For example, inhibition of SAH hydrolase results inhibition of viral mRNA methylation, thus inhibiting viral replication (Scheme 1).

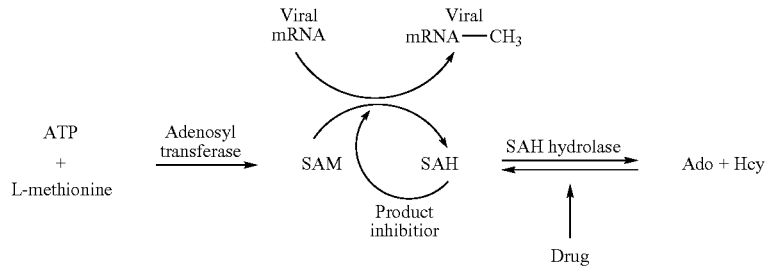

Numerous inhibitors of SAH hydrolase have been identified from naturally occurring compounds and synthetic compounds, including irreversible and reversible inhibitors. See, e.g., Yuan et al., *Exp. Opin. Ther. Patents*, 9: 1197-1206 (1999); Wolfe and Borchardt, *Journal of Medicinal Chemistry*, 34:1521-1530 (1991); Votruba and Holy, *Coll. Czech. Chem. Commun.*, 45:3039 (1980); Schanche et al., *Molecular Plarmacology*, 26:553-558 (1984); U.S. Ser. No. 10/410,879. It is an object of the invention to provide methods for screening inhibitors of SAH hydrolase.

S-adenosylmethionine (SAM)-dependent methyltransferase is an enzyme that catalyzes the transfer of a methyl group from SAM to a substrate and converts SAM to SAH. Methyltransferase, including SAM-dependent methyltransferase catalyzing abnormal methylation has been linked to pathological conditions (see, e.g., U.S. Pat. No. 5,876,996). For example, covalent modification of cellular substrates with methyl groups has been implicated in the pathology of cancer and other diseases (Gloria, et al., Cancer, 78:2300-2306 (1996)). Cytosine hypermethylation of eukaryotic DNA prevents transcriptional activation (Turker and Bestor, Mutat. Res., 386:119-130 (1997)). $N^6$-methyladenosine is found at internal positions of mRNA in higher eukaryotes (Bokar, et al., J. Biol. Chem., 269:17697-17704 (1994)). Hypermethylated viral DNA is transcribed at higher rates than hypo- or hemimethylated DNA in infected cells (Willis, et al. Cell. Biophys., 15:97-111 (1989)).

In addition, many pathways of small molecule degradation, such as those of neurotransmitters, require methyltransferase activity (U.S. Pat. No. 5,876,996; and Kagan and Clarke, Arch. Biochem. Biophys., 310:417427 (1994)). Degradation of catecholamines (epinephrine ornorepinephrine) requires phenylethanolamine N-methyltransferase. Hydroxyindole methyltransferase converts N-acetyl-5-hydroxytryptamine to melatonin in the pineal gland.

In their roles as a rate-limiting step in methyltransferase reactions, SAM-dependent methyltransferases have been identified as targets for psychiatric, antiviral, anticancer and anti-inflammatory drug design (U.S. Pat. No. 5,876,996). For instances, sequence-specific methylation inhibits the activity of the Epstein-Barr virus LMP1 and BCR2 enhancer-promoter regions (Minarovits et al., Virology, 200: 661-667 (1994)). 2'-5'-linked oligo(adenylic acid) nucleoside analogues synthesized by interferon-treated mouse L cells act as antiviral agents (Goswarmi, et al., J. Biol. Chem., 257:6867-6870 (1982)). Adenine analog inhibitors of AdoMet-MT decreased nucleic acid methylation and proliferation of leukemia L1210 cells (Kramer et al., Cancer Res., 50:3838-3842 (1990)). Therefore, another object of the invention is to provide methods for screening for inhibitors for SAM-dependent methyltransferases.

BRIEF SUMMARY OF THE INVENTION

In one aspect, the present invention provides a method for assaying of an inhibitor of a S-adenosylhomocysteine (SAH) hydrolase, said method comprises: a) contacting a SAH hydrolase with (i) SAH, (ii) a tracer, wherein the tracer is a labeled SAH or a labeled SAH analog and is not hydrolyzed by the SAH hydrolase, and (iii) in the presence or absence of a compound suspected of being an inhibitor of the SAH hydrolase under a condition that allows hydrolysis of the SAH into adenosine (Ado) and homocysteine (Hcy) catalyzed by the SAH hydrolase in the absence of an inhibitor of the SAH hydrolase; and wherein i) the tracer generates a detectable signal after binding to the SAH hydrolase or ii) the SAH hydrolase is immobilized on a suitable surface; b) detecting binding of the tracer to the SAH hydrolase; and c) comparing the amount of binding of the tracer to the SAH hydrolase in the presence of the compound to the amount of binding in the absence of the compound, whereby an increase in the amount of binding in the presence of the compound compared to the amount of binding in the absence of the compound indicates that the compound is an inhibitor of the SAH hydrolase.

In some embodiments, the SAH hydrolase and a mutant SAH hydrolase are contacted with (i) SAH, (ii) the tracer, and (iii) the compound suspected of being an inhibitor of SAH hydrolase in step a), wherein the mutant SAH hydrolase has binding affinity for SAH and adenosine but has attenuated catalytic activity; wherein i) the tracer generates a detectable signal after binding to the SAH hydrolase and the mutant SAH hydrolase or ii) the SAH hydrolase and mutant SAH hydrolase are immobilized on a suitable surface; wherein the binding detected in step b) is binding of the tracer to the SAH hydrolase and the mutant SAH hydrolase.

In some embodiments, the label of the tracer is a florescence. In some embodiments, the binding of the tracer to the SAH hydrolase (in some embodiments, including mutant SAH hydrolase) is detected by detecting the fluorescent polarization of the tracer.

In some embodiments, the method is conducted using a single SAH hydrolase and a single compound suspected of being an inhibitor of the SAH hydrolase in one assay. In other embodiments, the method is conducted in a high throughput screening mode, i.e., a plurality of the SAH hydrolases and/or a plurality of the compounds suspected of being inhibitors of the SAH hydrolases are screened simultaneously. The methods can be conducted in a multi-well (e.g., 24-, 48-, 96-, or 384-well), chip or array format. The SAH hydrolase (in some embodiments, including mutant SAH hydrolase) may be linked to a solid support, and may be arranged in an array on the solid support.

The invention also provides a kit for assaying for an inhibitor of a SAH hydrolase, said kit comprises (i) SAH, (ii) a tracer, wherein the tracer is a labeled SAH or a labeled SAH analog and is not hydrolyzed by the SAH hydrolase, and (iii) a SAH hydrolase, wherein the tracer generates a detectable signal after binding to the SAH hydrolase or the SAH hydrolase is immobilized on a suitable surface. In some embodiments, said kit further comprises a mutant SAH hydrolase, wherein the mutant SAH hydrolase has binding affinity for SAH and adenosine but has attenuated catalytic activity; and wherein the tracer generates a detectable signal after binding to the SAH hydrolase and the mutant SAH hydrolase, or the SAH hydrolase and the mutant SAH hydrolase are immobilized on a suitable surface.

In another aspect, the invention provides a method for assaying for an inhibitor of a S-adenosylmethionine (SAM)-dependent methyltransferase, comprising: a) contacting a SAM-dependent methyltransferase with (i) a substrate of the methyltransferase, (ii) SAM, and (iii) in the presence or absence of a compound suspected of being an inhibitor of the methyltransferase, under a condition that a methyl group is transferred from SAM to the substrate and SAM is converted to SAH; b) contacting the resulting SAH with a SAH hydrolase and a tracer under a condition that allows hydrolysis of the SAH into adenosine (Ado) and homocysteine (Hcy) catalyzed by the SAH hydrolase; wherein the tracer is a labeled SAH or a labeled SAH analog and is not hydrolyzed by the SAH hydrolase; and wherein i) the tracer generates a detectable signal after binding to the SAH hydrolase, or ii) the SAH hydrolase is immobilized on a suitable surface; c) detecting binding of the tracer to the SAH hydrolase; and d) comparing the amount of binding of the tracer to the SAH hydrolase in the presence of the compound to the amount of binding in the absence of the compound, whereby an increase in the amount of binding in the presence of the compound compared to the amount of binding in the absence of the compound indicates that the compound is an inhibitor of the SAM-dependent methyltransferase.

In some embodiments, the SAM-dependent methyltransferase is selected from the group consisting of a protein methyltransferase, a nucleic acid methyltransferase, a lipid methyltransferase, a polysaccharide methyltransferase and a small molecule methyltransferase. In some embodiments, the substrate is selected from a group consisting of a protein, a nucleic acid, a lipid, and a small molecule, and wherein the SAM-dependent methyltransferase is selected from the group consisting of a protein methyltransferase, a nucleic acid methyltransferase, a lipid methyltransferase, and a small molecule methyltransferase.

In some embodiments, the resulting SAH is contacted with the SAH hydrolase, a mutant SAH hydrolase, and the tracer; wherein the mutant SAH hydrolase has binding affinity for SAH and adenosine but has attenuated catalytic activity; wherein i) the tracer generates a detectable signal after binding to the SAH hydrolase and the mutant SAH hydrolase, or ii) the SAH hydrolase and the mutant SAH hydrolase are immobilized on a suitable surface; and wherein the binding detected in step c) is binding of the tracer to the SAH hydrolase and the mutant SAH hydrolase.

In some embodiments, the label of the tracer is a florescence. In some embodiments, the binding of the tracer to the SAH hydrolase (in some embodiments, including mutant SAH hydrolase) is detected by detecting the fluorescent polarization of the tracer.

In some embodiments, the method is conducted using a single SAM-dependent methyltransferase and a single compound suspected of being an inhibitor of the SAM-dependent methyltransferase in one assay. In other embodiments, the method is conducted in a high throughput screening mode, i.e., a plurality of the SAM-dependent methyltransferases and/or a plurality of the compounds suspected of being inhibitors of the SAM-dependent methyltransferases are screened simultaneously. The methods can be conducted in a multi-well (e.g., 24-, 48-, 96-, or 384-well), chip or array format. The SAH hydrolase (in some embodiments, including mutant SAH hydrolase) may be linked to a solid support, and may be arranged in an array on the solid support.

The invention also provides a kit for assaying for an inhibitor for S-adenosylmethionine (SAM)-dependent methyltransferase, comprising a SAM-dependent methyltransferase, a SAH hydrolase, and a tracer; wherein the tracer is a labeled SAH or a labeled SAH analog and is not hydrolyzed by the SAH hydrolase; and wherein i) the tracer generates a detectable signal after binding to the SAH hydrolase, or ii) the SAH hydrolase is immobilized on a suitable surface. In some embodiments, the kit further comprises a mutant SAH hydrolase, wherein the mutant SAH hydrolase has binding affinity for SAH and adenosine but has attenuated catalytic activity; and wherein the tracer generates a detectable signal after binding to the SAH hydrolase and the mutant SAH hydrolase, or the SAH hydrolase and the mutant SAH hydrolase are immobilized on a suitable surface.

In the system assaying for inhibitors of SAH hydrolase, an increase of the tracer binding would be observed when an inhibitor of SAH hydrolase is present in the assay system. In the system for assaying inhibitors of SAM-dependent methyltransferase, an increase of the tracer binding would be observed when an inhibitor of SAM-dependent methyltransferase is present in the assay system.

DETAILED DESCRIPTION OF THE INVENTION

Figure 1:
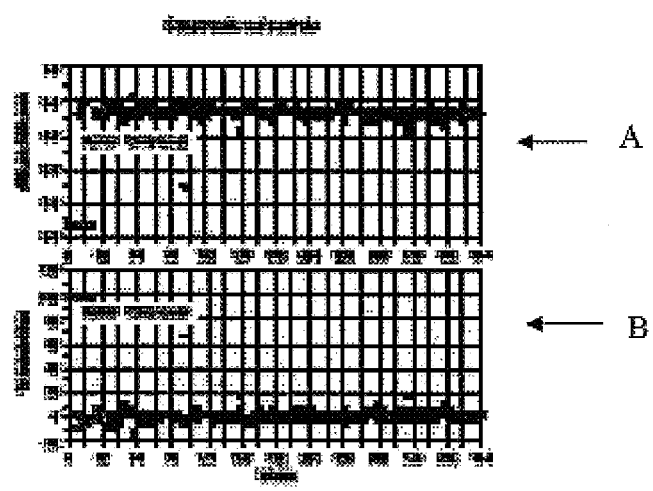
FIG. 1A is a graph showing fluorescence polarization of the assay described in Example 2 where a compound with good inhibitory activity against histone methyltransferase was present in the assay.
FIG. 1B is a graph showing fluorescence polarization of the assay described in Example 2 where a compound without inhibitory activity against histone methyltransferase was present in the assay. The X axis corresponds to time (min); and the Y axis corresponds to fluorescence polarization.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "SAH hydrolase" refers to an ubiquitous eukaryotic enzyme, which is also found in some prokaryotes, which catalyzes hydrolysis of SAH to adenosine (Ado) and Hcy. SAH hydrolase also catalyzes the formation of SAH from Ado and Hcy. The co-enzyme of SAH hydrolase is $NAD^+$/NADH. SAH hydrolase may have several catalytic activities. In the hydrolytic direction, the first step involves oxidation of the 3'-hydroxyl group of SAH (3'-oxidative activity) by enzyme-bound $NAD^+$ ($E-NAD^+$), followed by β-elimination of L-Hcy to give 3'-keto-4',5'-didehydro-5'-deoxy-Ado. Michael addition of water to the 5'-position to this tightly bound intermediate (5'-hydrolytic activity) affords 3'-keto-Ado, which is then reduced by enzyme-bound NADH (E-NADH) to Ado (3'-reduction activity). It is intended to encompass SAH hydrolase with conservative amino acid substitutions that do not substantially alter its activity.

As used herein, "mutant SAH hydrolase, wherein said mutant SAH hydrolase has binding affinity for SAH and adenosine but has attenuated catalytic activity" refers to a mutant form of SAH hydrolase that retains sufficient binding affinity for SAH and adenosine to be detected in the process or method, particularly assay, of interest. Typically this is at least about 10%, preferably at least about 50% binding affinity for SAH and adenosine, compared to its wildtype counterpart SAH hydrolase. Preferably, such mutant SAH hydrolase retains 60%, 70%, 80%, 90%, 100% binding affinity for SAH and adenosine compared to its wildtype counterpart for SAH and adenosine, or has a higher binding affinity than its wildtype counterpart for SAH and adenosine. Such mutant SAH hydrolase can be herein referred to as a "substrate trapping SAH and adenosine," i.e., a molecule that specifically binds to SAH and adenosine, but does not catalyze conversion therebetween.

As used herein, "attenuated catalytic activity" refers to a mutant SAH hydrolase that retains sufficiently reduced catalytic activity to be useful in the present method. The precise reduction in catalytic activity for use in the assays can be empirically determined for each assay. Typically, the enzyme will retain less than about 50% of one of its catalytic activities or less than 50% of its overall catalytic activities compared to its wildtype counterpart. Preferably, a mutant SAH hydrolase retains less than 40%, 30%, 20%, 10%, 1%, 0.1%, or 0.01% of one of its catalytic activities or its overall catalytic activities compared to its wildtype counterpart. More preferably, a mutant SAH hydrolase lacks detectable level of one of its catalytic activities or its overall catalytic activities compared to its wildtype counterpart.

As used herein, "homocysteine (Hcy)" refers to a compound with the following molecular formula: $HSCH_2CH_2CH(NH_2)COOH$. Biologically, Hcy is produced by demethylation of methionine and is an intermediate in the biosynthesis of cysteine from methionine. The term "Hcy" encompasses free Hcy (in the reduced form) and conjugated Hcy (in the oxidized form). Hcy can conjugate with proteins, peptides, itself or other thiols through disulfide bond.

As used herein, "S-adenosylmethionine (SAM)-dependent methyltransferase" refers to an enzyme that transfers a methyl group from SAM to a substrate and converts SAM to S-adenosylhomocysteine (SAH). SAM-dependent methyltransferase can transfer a methyl group from SAM to a carbon, an oxygen, a nitrogen or a sulfur atom of a substrate, and the SAM-dependent methyltransferase is thereby further classified as a C—, O—, N—, or S-methyltransferase, respectively. Any such SAM-dependent methyltransferase, including those with conservative amino acid substitutions that do not substantially alter its activity are contemplated herein.

As used herein, "substrate of a SAM-dependent methyltransferase" refers to a substance that receives the methyl group from SAM in a reaction catalyzed by the SAM-dependent methyltransferase. Examples of the substrates of the SAM-dependent methyltransferases include proteins, nucleic acids, lipids, polysaccharides and other small molecules. As used herein, "SAM" is not considered a "substrate of a SAM-dependent methyltransferase."

As used herein, "protein SAM-dependent methyltransferase" refers to an enzyme that transfers a methyl group from SAM to a protein substrate and converts SAM to SAH.

As used herein, "nucleic acid SAM-dependent methyltransferase" refers to an enzyme that transfers a methyl group from SAM to a nucleic acid substrate, such as a DNA or a RNA, and converts SAM to SAH.

As used herein, "lipid SAM-dependent methyltransferase" refers to an enzyme that transfers a methyl group from SAM to a lipid substrate and converts SAM to SAH.

As used herein, "polysaccharide SAM-dependent methyltransferase" refers to an enzyme that transfers a methyl group from SAM to a polysaccharide substrate and converts SAM to SAH.

As used herein, "small molecule SAM-dependent methyltransferase" refers to an enzyme that transfers a methyl group from SAM to a small molecule substrate and converts SAM to SAH.

In all instances the methyltransferases encompass variants and mutants thereof, particularly those with conservative amino acid substitutions (see, e.g., TABLE 1, below), that retain the methyltransferring activity. Such substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, "small molecule" refers to a molecule that, without forming homo-aggregates or without attaching to a macromolecule or adjuvant, is incapable of generating an antibody that specifically binds to the small molecule. Preferably, the small molecule has a molecule weight that is about or less than 10,000 daltons. More preferably, the small molecule has a molecule weight that is about or less than 5,000 Dalton.

As used herein, "enzyme" refers to a protein specialized to catalyze or promote a specific metabolic reaction. Generally, enzymes are catalysts, but for purposes herein, such "enzymes" include those that would be modified during a reaction. Since the enzymes are modified to eliminate or substantially eliminate catalytic activity, they will not be so-modified during a reaction.

As used herein, "SAM-dependent homocysteine S-methyltransferase" refers to an enzyme that catalyzes formation of methionine and S-adenosyl-L-homocysteine (SAH) from homocysteine and S-adenosylmethionine (SAM). It is intended to encompass SAM-dependent homocysteine S-methyltransferase with conservative amino acid substitutions that do not substantially alter its activity.

As used herein, high-throughput screening (HTS) refers to processes that test a large number of compounds, such as compounds of diverse chemical structures against disease targets to identify "hits" (see, e.g., Broach, et al., High throughput screening for drug discovery, *Nature*, 384:14-16 (1996); Janzen, et al., High throughput screening as a discovery tool in the pharmaceutical industry, *Lab Robotics Automation*: 8261-265 (1996); Fernandes, P. B., Letter from the society president, *J. Biomol. Screening*, 2:1 (1997); Burbaum, et al., New technologies for high-throughput screening, *Curr. Opin. Chem. Biol.*, 1:72-78 (1997)]. HTS operations are highly automated and computerized to handle sample preparation, assay procedures and the subsequent processing of large volumes of data.

B. Methods and Kits for Assaying Inhibitors of SAH Hydrolase

The invention provides methods for screening compounds that inhibit SAH hydrolase activity. These compounds can be potential drugs for treating various conditions and diseases.

In one aspect, the invention provides a method for assaying for an inhibitor of a S-adenosylhomocysteine (SAH) hydrolase, said method comprises: a) contacting a SAH hydrolase with (i) SAH, (ii) a tracer, wherein the tracer is a labeled SAH or a labeled SAH analog and is not hydrolyzed by the SAH hydrolase, and (iii) in the presence or absence of a compound suspected of being an inhibitor of the SAH hydrolase under a condition that allows hydrolysis of the SAH into adenosine (Ado) and homocysteine (Hcy) catalyzed by the SAH hydrolase in the absence of an inhibitor of the SAH hydrolase; and wherein i) the tracer generates a detectable signal after binding to the SAH hydrolase or ii) the SAH hydrolase is immobilized on a suitable surface; b) detecting binding of the tracer to the SAH hydrolase; and c) comparing the amount of binding of the tracer to the SAH hydrolase in the presence of the compound to the amount of binding in the absence of the compound, whereby an increase in the amount of binding in the presence of the compound compared to the amount of binding in the absence of the compound indicates that the compound is an inhibitor of the SAH hydrolase.

The assay may be conducted in the presence of a mutant SAH hydrolase. In these embodiments, the SAH hydrolase and a mutant SAH hydrolase are contacted with (i) SAH, (ii) the tracer, and (iii) the compound suspected of being an inhibitor of SAH hydrolase in step a), wherein the mutant SAH hydrolase has binding affinity for SAH and adenosine but has attenuated catalytic activity; wherein i) the tracer generates a detectable signal after binding to the SAH hydrolase and the mutant SAH hydrolase or ii) the SAH hydrolase and mutant SAH hydrolase are immobilized on a suitable surface; and the binding detected in step b) is binding of the tracer to the SAH hydrolase and the mutant SAH hydrolase.

1. SAH Hydrolase and Mutant SAH Hydrolase

The methods of the invention may be used to screen inhibitors of any SAH hydrolase. In some embodiments, the methods may be used to screen inhibitors of SAH hydrolase encoded by the following nucleic acid sequences having the GenBank Accession Nos.: AF129871 (*Gossypium hirsutum*); AQ003753 (*Cryptosporidium parvum*); AF105295 (*Alexandrium fundyense*); AA955402 (*Rattus norvegicus*); AA900229 (*Rattus norvegicus*); AA874914 (*Rattus norvegicus*); AA695679 (*Drosophila melanogaster* ovary); AA803942 (*Drosophila melanogaster* ovary; AI187655 (*Manduca sexta* male antennae); U40872 (*Trichomonas vaginalis*); AJ007835 (*Xenopus Laevis*); AF080546 (*Anopheles gambiae*); AI069796 (*T. cruzi* epimastigote); Z97059 (*Arabidopsis thaliana*); AF059581 (*Arabidopsis thaliana*); U82761 (*Homo sapiens*); AA754430 (*Oryza sativa*); D49804 (*Nicotiana tabacum*); D45204 (*Nicotiana tabacum*); X95636 (*D. melanogaster*); T18277 (endosperm Zea mays); R75259 (Mouse brain); Z26881 (*C. roseus*); X12523 (*D. discoideum*); X64391 (*Streptomyces fradiae*); W21772 (Maize Leaf); AH003443 (*Rattus norvegicus*); U14963 (*Rattus norvegicus*); U14962 (*Rattus norvegicus*); U14961 (*Rattus norvegicus*); U14960 (*Rattus norvegicus*); U14959 (*Rattus norvegicus*); U14937 (*Rattus norvegicus*); U14988 (*Rattus norvegicus*); U14987 (*Rattus norvegicus*); U14986 (*Rattus norvegicus*); U14985 (*Rattus norvegicus*);

U14984 (*Rattus norvegicus*); U14983 (*Rattus norvegicus*); U14982 (*Rattus norvegicus*); U14981 (*Rattus norvegicus*); U14980 (*Rattus norvegicus*); U14979 (*Rattus norvegicus*); U14978 (*Rattus norvegicus*); U14977 (*Rattus norvegicus*); U14976 (*Rattus norvegicus*); U14975 (*Rattus norvegicus*); L32836 (*Mus musculus*); L35559 (*Xenopus laevis*); Z19779 (Human foetal Adrenals tissue); L23836 (*Rhodobacter capsulatus*); M15185 (Rat); L11872 (*Triticum aestivum*); M19937 (Slime mold (*D. discoideum*); M80630 (*Rhodobacter capsulatus*). In other embodiments, inhibitors of SAH hydrolase (human placental SAH hydrolase) encoded by the nucleotide sequences with the GenBank accession Nos. M61831-61832 are assayed using the methods of the invention. See also Coulter-Karis and Hershfield, *Ann. Hum. Genet.*, 53(2):169-175 (1989)). In other embodiments, inhibitors of SAH hydrolase descried in U.S. Pat. No. 5,854,023 are assayed.

Any mutant SAH hydrolase that substantially retains its binding affinity or has enhanced binding affinity for SAH and adenosine (Ado), but has attenuated catalytic activity can be used in the methods of the invention. Mutant enzyme can be prepared using mutagenesis methods after obtaining nucleic acid encoding SAH hydrolase.

Nucleic acids encoding SAH hydrolase can be obtained by methods known in the art. Additional nucleic acid molecules encoding such enzymes are known and the molecules or sequences thereof are publicly available. If the molecules are available they can be used; alternatively the known sequences can be used to obtain clones from selected or desired sources. For example, the nucleic acid sequences of SAH hydrolases can be used in isolating nucleic acids encoding SAH hydrolases from natural sources. Alternatively, nucleic acids encoding SAH hydrolases can be obtained by chemical synthesis according to the known sequences.

Once nucleic acids encoding SAH hydrolases are obtained, these nucleic acids can be mutagenized and screened and/or selected for mutant SAH hydrolase having binding affinity for SAH and adenosine but having attenuated catalytic activity. Insertion, deletion, or point mutation(s) can be introduced into nucleic acids encoding SAH hydrolases according to methods known to those of skill in the art. Information regarding the structural-functional relationship of the SAH hydrolases can be used in the mutagenesis and selection of mutant SAH hydrolase having binding affinity for SAH and adenosine but having attenuated catalytic activity.

In one example, the mutant SAH hydrolase used in the method has a mutation in an amino acid residue that is directly involved in the SAH hydrolase's catalytic activity, its binding with $NAD^+$, NADH, Hcy, SAH or adenosine. In another example, the mutant SAH hydrolase used in the method has a mutation in an amino acid residue that is adjacent to an amino acid residue that is directly involved in the SAH hydrolase's catalytic activity, its binding with $NAD^+$, NADH, Hcy, SAH or adenosine. Information on the SAH hydrolase's catalytic domain, various binding domains including the NAD binding domain and conserved amino acid residues are generally known and can be used in the designing of a suitable mutant SAH hydrolase (See e.g., Turner et al., *Nat. Struct. Biol.*, 5(5):369-76 (1998) entitled "Structure determination of selenomethionyl S-adenosylhomocysteine hydrolase using data at a single wavelength;" Yin et al., *Biomedical Chemistry: Applying Chemical Principles to the Understanding and Treatment of Disease* (Ed. Torrence), Chapter 2, Mechanism-based S-adenosylhomocysteine hydrolase inhibitors in the search for broad-spectrum antiviral agents), John Wiley & Sons, Inc. (2000); Hu et al., *Biochemistry*, 38(26):8323-33 (1999) entitled "Crystal structure of S-adenosylhomocysteine hydrolase from rat liver;" Creedon et al., *J. Biol. Chem.*, 269(23): 16364-70 (1994) entitled "*Plasmodium falciparum* S-adenosylhomocysteine hydrolase. cDNA identification, predicted protein sequence, and expression in *Escherichia coli.*;" and Henderson et al., *Mol. Biochem. Parasitol.*, 53(1-2): 169-83 (1992) entitled "Cloning of the gene encoding *Leishmania donovani* S-adenosylhomocysteine hydrolase, a potential target for antiparasitic chemotherapy."

Once a mutant SAH hydrolase with desired properties, i.e., substantially retaining binding affinity for SAH and adenosine but having attenuated catalytic activity, is identified, such mutant SAH hydrolase can be produced by any methods known in the art including recombinant expression, chemical synthesis or a combination thereof. Preferably, the mutant SAH hydrolase is obtained by recombinant expression.

SAH hydrolase from mammalian sources are homotetramer of approximate molecular weight of 180-190 KD. The enzyme contains 4 molecules of tightly-bound $NAD^+$ as a co-enzyme. The catalytic mechanism of the enzyme in the hydrolytic direction includes two consecutive reactions, i.e., the 3'-oxidation of the substrate to 3'-keto in concomitant with the reduction of the enzyme-bound NAD+ to NADH, and followed by the 5'-hydrolysis to release the reaction products Hcy and Ado (Refsum, et al., *Clin. Chem.*, 31:624-628 (1985)). The C-terminal regions of all known SAH hydrolase are extremely conserved and contain essential amino acid residues to the enzyme catalysis. The crystal structure of human SAH hydrolase in complex with a substrate analog inhibitor was recently determined. This x-ray structure of SAH hydrolase indicates that at least twenty amino acid residues are directly or indirectly interacting with the substrate analog inhibitor and co-enzyme $NAD^+$. Mutations of those amino acid residues that are involved directly or indirectly in the substrate binding and catalysis can readily be made by site-directed mutagenesis, and the sequence of the resulting mutant enzyme can be confirmed by comparing the mutant SAH hydrolase DNA sequence with the sequence of the wild type enzyme to ensure no other mutations are introduced to the specific mutant enzyme.

Any mutant SAH hydrolase described in U.S. Ser. No. 10/043,787 (filed Jan. 10, 2002) may be used. In one specific embodiment, the attenuated catalytic activity of the mutant SAH hydrolase is caused by mutation(s) in the mutant SAH hydrolase's binding site for $NAD^+$, or mutation(s) in the mutant SAH hydrolase's catalytic site or a combination thereof. In another specific embodiment, the mutant SAH hydrolase has attenuated 5'-hydrolytic activity but substantially retains its 3'-oxidative activity. In still another specific embodiment, the mutant SAH hydrolase irreversibly binds SAH. In yet another specific embodiment, the mutant SAH hydrolase has a Km for SAH that is about or less than 10.0 µM. Preferably, the mutant SAH hydrolase has a Km for SAH that is about 1.0 µM or less than 1.0 µM. In yet another specific embodiment, the mutant SAH hydrolase has a Kcat for SAH that is about or less than 0.1 $S^{-1}$.

In yet another specific embodiment, the mutant SAH hydrolase has one or more insertion, deletion, or point mutation(s). Preferably, the mutant SAH hydrolase is derived from the sequence of amino acids set forth in SEQ ID NO:1 (TABLE 2) or encoded by the sequence of nucleotides set forth in SEQ ID NO:2 (TABLE 3) but has one or more of the following mutations: R38E, C53S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, I240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A, Y432F, and deletion of Tyr 432 (Δ432). Also more preferably, the mutant SAH hydrolase is a derived sequence of amino acids set forth in SEQ ID NO:1 or encoded by the sequence of nucleotides set forth in SEQ ID NO:2 and has a combination of Arg 431 to Ala (R431A) and Lys 426 to Arg (K426R) mutations. The nucleic acid molecules contemplated also include those that have conservative amino acid changes, and include those that hybridize along their full length to the coding portion of the sequence of nucleotides set forth in SEQ ID NO:2, under medium stringency, or preferably high stringency, such that the encoded protein retains ability to bind to the selected analyte without substantial conversion of the analyte.

TABLE 2

Human placental SAH hydrolase amino acid sequence (SEQ ID NO:1)

| Met 1 | Ser | Asp | Lys | Leu 5 | Pro | Tyr | Lys | Val | Asp 10 | Ile | Gly | Leu | Ala | Ala 15 |
|---|---|---|---|---|---|---|---|---|---|---|---|---|---|---|
| Trp | Gly | Arg | Lys 20 | Ala | Leu | Asp | Ile | Ala 25 | Glu | Asn | Glu | Met | Pro 30 | Gly | Leu |
| Met | Arg | Met 35 | Arg | Glu | Arg | Tyr | Ser 40 | Ala | Ser | Lys | Pro | Leu 45 | Lys | Gly | Ala |
| Arg | Ile 50 | Ala | Gly | Cys | Leu | His 55 | Met | Thr | Val | Glu | Thr 60 | Ala | Val | Leu | Ile |
| Glu 65 | Thr | Leu | Val | Thr | Leu 70 | Gly | Ala | Glu | Val | Gln 75 | Trp | Ser | Ser | Cys | Asn 80 |
| Ile | Phe | Ser | Thr | Gln 85 | Asn | His | Ala | Ala | Ala 90 | Ile | Ala | Lys | Ala | Gly 95 |
| Ile | Pro | Val | Tyr 100 | Ala | Trp | Lys | Gly | Glu 105 | Thr | Asp | Glu | Glu | Tyr 110 | Leu | Trp |
| Cys | Ile | Glu | Gln 115 | Thr | Leu | Tyr | Phe 120 | Lys | Asp | Gly | Pro | Leu 125 | Asn | Met | Ile |
| Leu | Asp | Asp 130 | Gly | Gly | Asp | Leu 135 | Thr | Asn | Leu | Ile | His 140 | Thr | Lys | Tyr | Pro |
| Gln | Leu 145 | Leu | Pro | Gly | Ile | Arg 150 | Gly | Ile | Ser | Glu | Glu 155 | Thr | Thr | Thr | Gly 160 |
| Val | His | Asn | Leu | Tyr 165 | Lys | Met | Met | Ala | Asn 170 | Gly | Ile | Leu | Lys | Val 175 | Pro |
| Ala | Ile | Asn | Val 180 | Asn | Asp | Ser | Val | Thr 185 | Lys | Ser | Lys | Phe | Asp 190 | Asn | Leu |
| Tyr | Gly | Cys 195 | Arg | Glu | Ser | Leu | Ile 200 | Asp | Gly | Ile | Lys | Arg 205 | Ala | Thr | Asp |
| Val | Met | Ile 210 | Ala | Gly | Lys | Val 215 | Ala | Val | Val | Ala | Gly 220 | Tyr | Gly | Asp | Val |
| Gly 225 | Lys | Gly | Cys | Ala | Gln 230 | Ala | Leu | Arg | Gly | Phe 235 | Gly | Ala | Arg | Val | Ile 240 |
| Ile | Thr | Glu | Ile | Asp 245 | Pro | Ile | Asn | Ala | Leu 250 | Gln | Ala | Ala | Met | Glu 255 | Gly |
| Tyr | Glu | Val | Thr 260 | Thr | Met | Asp | Glu | Ala 265 | Cys | Gln | Glu | Gly | Asn 270 | Ile | Phe |
| Val | Thr | Thr 275 | Thr | Gly | Cys | Ile | Asp 280 | Ile | Ile | Leu | Gly | Arg 285 | His | Phe | Glu |
| Gln | Met 290 | Lys | Asp | Asp | Ala | Ile 295 | Val | Cys | Asn | Ile | Gly 300 | His | Phe | Asp | Val |
| Glu | Ile 305 | Asp | Val | Lys | Trp | Leu 310 | Asn | Glu | Asn | Ala | Val 315 | Glu | Lys | Val | Asn 320 |
| Ile | Lys | Pro | Gln | Val 325 | Asp | Arg | Tyr | Arg | Leu 330 | Lys | Asn | Gly | Arg | Arg 335 | Ile |

TABLE 2-continued

Human placental SAH hydrolase amino acid sequence (SEQ ID NO:1)

Ile Leu Leu Ala Glu Gly Arg Leu Val Asn Leu Gly Cys Ala Met Gly
            340                 345                 350

His Pro Ser Phe Val Met Ser Asn Ser Phe Thr Asn Gln Val Met Ala
            355                 360                 365

Gln Ile Glu Leu Trp Thr His Pro Asp Lys Tyr Pro Val Gly Val His
    370                 375                 380

Phe Leu Pro Lys Lys Leu Asp Glu Ala Val Ala Glu Ala His Leu Gly
385                 390                 395                 400

Lys Leu Asn Val Lys Leu Thr Lys Leu Thr Glu Lys Gln Ala Gln Tyr
                405                 410                 415

Leu Gly Met Ser Cys Asp Gly Pro Phe Lys Pro Asp His Tyr Arg Tyr
            420                 425                 430

TABLE 3

Human placental SAH hydrolase nucleotide sequence (SEQ ID NO:2)

| | |
|---|---|
| ctgaggccca gccccttcg cccgtttcca tcacgagtgc cgccagcatg tctgacaaac | 60 |
| tgccctacaa agtcgccgac atcggcctgg ctgcctgggg acgcaaggcc ctggacattg | 120 |
| ctgagaacga gatgccgggc ctgatgcgta tgcgggagcg gtactcggcc tccaagccac | 180 |
| tgaagggcgc ccgcatcgct ggctgcctgc acatgaccgt ggagacggcc gtcctcattg | 240 |
| agaccctcgt caccctgggt gctgaggtgc agtggtccag ctgcaacatc ttctccaccc | 300 |
| agaaccatgc ggcggctgcc attgccaagg ctggcattcc ggtgtatgcc tggaagggcg | 360 |
| aaacggacga ggagtacctg tggtgcattg agcagaccct gtacttcaag gacgggcccc | 420 |
| tcaacatgat tctggacgac gggggcgacc tcaccaacct catccacacc aagtacccgc | 480 |
| agcttctgcc aggcatccga ggcatctctg aggagaccac gactggggtc cacaacctct | 540 |
| acaagatgat ggccaatggg atcctcaagg tgcctgccat caatgtcaat gactccgtca | 600 |
| ccaagagcaa gtttgacaac tctctatggct gccgggagtc cctcatagat ggcatcaagc | 660 |
| gggccacaga tgtgatgatt gccggcaagg tagcggtggt agcaggctat ggtgatgtgg | 720 |
| gcaagggctg tgcccaggcc ctgcggggtt tcggagcccg cgtcatcatc accgagattg | 780 |
| acccatcaa cgcactgcag gctgccatgg agggctatga ggtgaccacc atggatgagg | 840 |
| cctgtcagga gggcaacatc tttgtcacca ccacaggctg tattgacatc atccttggcc | 900 |
| ggtaggtgcc agatgggggg tcccggggag tgagggagga gggcagagtt gggacagctt | 960 |
| tctgtccctg acaatctccc acggtcttgg gctgcctgac aggcactttg agcagatgaa | 1020 |
| ggatgatgcc attgtgtgta acattggaca ctttgacgtg gagatcgatg tcaagtggct | 1080 |
| caacgagaac gccgtggaga aggtgaacat caagccgcag gtggaccggt atcggttgaa | 1140 |
| gaatgggcgc cgcatcatcc tgctggccga gggtcggctg gtcaacctgg gttgtgccat | 1200 |
| gggccacccc agcttcgtga tgagtaactc cttcaccaac caggtgatgg cgcagatcga | 1260 |
| gctgtggacc catccagaca agtaccccgt tggggttcat ttcctgccca agaagctgga | 1320 |
| tgaggcagtg gctgaagccc acctgggcaa gctgaatgtg aagttgacca agctaactga | 1380 |
| gaagcaagcc cagtacctgg gcatgtcctg tgatggcccc ttcaagccgg atcactaccg | 1440 |
| ctactgagag ccaggtctgc gtttcaccct ccagctgctg tccttgccca ggccccacct | 1500 |
| ctcctcccta agagctaatg gcaccaactt tgtgattggt ttgtcagtgt ccccatcga | 1560 |

TABLE 3-continued

Human placental SAH hydrolase nucleotide sequence (SEQ ID NO:2)

```
ctctctgggg ctgatcactt agtttttggc ctctgctgca gccgtcatac tgttccaaat  1620
gtggcagcgg gaacagagta ccctcttcaa gccccggtca tgatggaggt cccagccaca  1680
gggaaccatg agctcagtgg tcttggaaca gctcactaag tcagtccttc cttagcctgg  1740
aagtcagtag tggagtcaca aagcccatgt gttttgccat ctaggccttc acctggtctg  1800
tggacttata cctgtgtgct tggtttacag gtccagtggt tcttcagccc atgacagatg  1860
agaaggggct atattgaagg gcaaagagga actgttgttt gaattttcct gagagcctgg  1920
cttagtgctg ggccttctct taaacctcat tacaatgagg ttagtacttt tagtccctgt  1980
tttacagggg ttagaataga ctgttaaggg gcaactgaga aagaacagag aagtgacagc  2040 tagggggttga gaggggccag aaaaacatga atgcaggcag atttcgtgaa atctgccacc  2100
actttataac cagatggttc ctttcacaac cctgggtcaa aaagagaata atttggccta  2160
taatgttaaa agaaagcagg aaggtgggta aataaaaatc ttggtgcctg g           2211
```

Nucleic acid encoding mutant SAH hydrolase may be cloned into expression vectors and transferred into any host cells. The recombinant host cell can be any suitable host cell, including, but not limited to, a bacterial cell, a yeast cell, a fungal cell, a plant cell, an insect cell or an animal cell. The recombinant host cells can be grown or cultured under conditions whereby the mutant SAH hydrolase is expressed by the cell. The expressed mutant SAH hydrolase can then be isolated or recovered.

2. Immobilization of SAH Hydrolase and Mutant SAH Hydrolase

In the methods for assaying inhibitors of SAH hydrolase, the SAH hydrolase and/or the mutant SAH hydrolase may be immobilized on a surface of a support, either directly or via a linker. In some embodiments, the support used is an insoluble support such as a silicon chip. Non-limiting examples of the geometry of the support include beads, pellets, disks, capillaries, hollow fibers, needles, solid fibers, random shapes, thin films, membranes and chips. In some embodiments, the SAH hydrolase and/or the mutant SAH hydrolase are immobilized in an array or a well format on the surface.

In certain embodiments, where the facilitating agents are designed for linkage to surfaces, the SAH hydrolase and/or the mutant SAH hydrolase can be attached to a surface of a matrix material. Immobilization may be effected directly or via a linker. The SAH hydrolase and/or the mutant SAH hydrolase may be immobilized on any suitable support, including, but are not limited to, silicon chips, and other supports described herein and known to those of skill in the art. A plurality of SAH hydrolase and/or mutant SAH hydrolase, which may contain the same or different or a variety thereof, may be attached to a support, such as an array (i.e., a pattern of two or more) on the surface of a silicon chip or other chip for use in high throughput protocols and formats.

It is also noted that the SAH hydrolase and/or the mutant SAH hydrolase can be linked directly to the surface or via a linker without a facilitating agent linked thereto. Hence chips containing arrays of the SAH hydrolase and/or the mutant SAH hydrolase are contemplated.

The matrix material substrates contemplated herein are generally insoluble materials used to immobilize ligands and other molecules, and are those that used in many chemical syntheses and separations. Such substrates, also called matrices, are used, for example, in affinity chromatography, in the immobilization of biologically active materials, and during chemical syntheses of biomolecules, including proteins, amino acids and other organic molecules and polymers. The preparation of and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

The substrate matrices are typically insoluble materials that are solid, porous, deformable, or hard, and have any required structure and geometry, including, but not limited to: beads, pellets, disks, capillaries, hollow fibers, needles, solid fibers, random shapes, thin films and membranes. Thus, the item may be fabricated from the matrix material or combined with it, such as by coating all or part of the surface or impregnating particles.

Typically, when the matrix is particulate, the particles are at least about 10-2000 μM, but may be smaller or larger, depending upon the selected application. Selection of the matrices will be governed, at least in part, by their physical and chemical properties, such as solubility, functional groups, mechanical stability, surface area swelling propensity, hydrophobic or hydrophilic properties and intended use.

Any support matrix material known in the art can be used. Examples of such material are described in U.S. Pat. No. 6,610,504. Any known methods for the immobilization of proteins and other biomolecules onto support matrix material may be used for immobilization. Examples of such methods are described in U.S. Pat. No. 6,610,504.

3. Tracer and Detection of Binding of the Tracer to SAH Hydrolase and/or Mutant SAH Hydrolase The tracer used for the methods of the invention is a labeled SAH or a labeled SAH analog or derivative which binds to SAH hydrolase but is not hydrolyzed by the SAH hydrolase.

A label is generally a moiety capable of producing a detectable signal, such as fluorophores, chromophores, radiolabels, enzymes, luminescent (including chemo- or bio-luminescent), and other labels used in immunoassays that can be conjugated to SAH or SAH analogs. Exemplary fluorophores are fluorescein, rhodamine, cyanine dyes, e.g., Cy2, Cy3, Cy3.5, Cy5, Cy5.5, texas red, and their derivatives.

An example of labeled SAH analog is a fluorescence labeled S-adenosylcysteine as described in U.S. Ser. No. 10/043,787 filed Jan. 10, 2002 and WO 03/060478. Methods of making the fluorescence labeled S-adenosylcysteine is also described in WO 03/060478.

Other examples of SAH analogs include molecules having the formula (I) shown below.

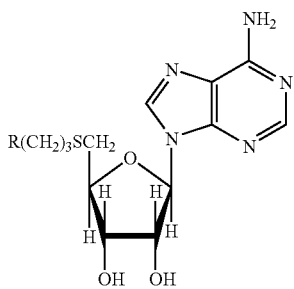

where R is an amine or carboxyl moiety or a salt or ester (e.g. with a $C_{1-4}$ alkanol) thereof, may be coupled to a molecule, such as a label. An example of a compound of formula I is shown below.

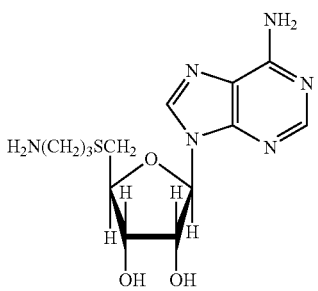

Other examples of SAH analogs include molecules having the formula (II) shown below.

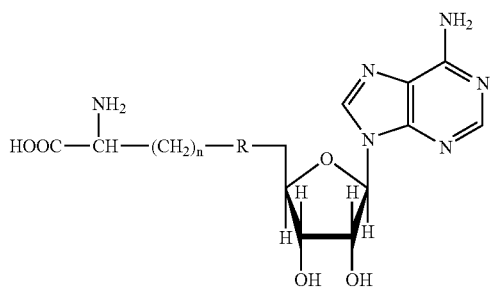

wherein R is oxygen or sulfur, and n is 0, 1, 2, 3, 4, or 5. The —COOH and/or —NH$_2$ moiety on the alkyl chain of formula II may be attached or coupled to a label.

Any detection technologies may be used to detect binding of the tracer to SAH hydrolase and/or mutant SAH hydrolase depending on the type of labels used for the tracer. For example, the binding of the fluorescent labeled SAH or SAH analogs to SAH hydrolase and mutant SAH hydrolase may be detected using fluorescence polarization technique (Jameson et al., Methods Enzymol., 246:283-300 (1995); Lundblad et al., Mol. Endocrinol., 10:607-612 (1996); Checovich et al., Nature, 375:254-256 (1995); Levine et al., Anal. Biochem., 247:83-88 (1997); Jolley, J. Biomol. Screening, 1:33-38 (1996); Schade et al., Anal. Biochem., 243:1-7 (1996); and Lynch et al., Anal. Biochem., 247:77-82 (1997)). When fluorescently labeled molecules in solution are illuminated with plane-polarized light, the emitted fluorescence will be in the same plane provided the molecules remain stationary. Since all molecules tumble as a result of collisional motion, depolarization phenomenon is proportional to the rotational relaxation time ($\mu$) of the molecule, which is defined by the expression $3\eta V/RT$. At constant viscosity ($\eta$) and temperature (T) of the solution, polarization is directly proportional to the molecular volume (V) (R is the universal gas constant). Hence changes in molecular volume or molecular weight due to binding interactions can be detected as a change in polarization. For example, the binding of a fluorescently labeled ligand to its receptor will result in significant changes in measured fluorescence polarization values for the ligand. Once again, the measurements can be made in a "mix and measure" mode without physical separation of the bound and free ligands. The polarization measurements are relatively insensitive to fluctuations in fluorescence intensity when working in solutions with moderate optical intensity.

The SAH hydrolase and/or the mutant SAH hydrolase may be immobilized on a suitable surface, and binding of the tracer to the SAH hydrolase and/or the mutant SAH hydrolase may be detected by washing away unbound and nonspecifically bound tracer after the enzymatic reaction and measuring the binding of the tracer to the immobilized SAH hydrolase and/or mutant SAH hydrolase.

4. High Throughput Screening Format

Although the assay methods described herein can be conducted using a single SAH hydrolase, and/or a single test substance in one assay, the assay preferably is conducted in a high throughput screening mode, i.e., a plurality of the SAH hydrolase are screened and/or a plurality of test substances are screened simultaneously (See generally, High Throughput Screening: The Discovery of Bioactive Substances (Devlin, Ed.) Marcel Dekker, 1997; Sittampalam et al., Curr. Opin. Chem. Biol., 1(3):384-91 (1997); and Silverman et al., Curr. Opin. Chem. Biol., 2(3):397-403 (1998)). For example, the assay can be conducted in a multi-well (e.g., 24-, 48-, 96-, or 384-well), chip or array format.

High-throughput screening (HTS) is the process of testing a large number of diverse chemical structures against disease targets to identify "hits" (Sittampalam et al., Curr. Opin. Chem. Biol., 1(3):384-91 (1997)). Current state-of-the-art HTS operations are highly automated and computerized to handle sample preparation, assay procedures and the subsequent processing of large volumes of data. Each one of these steps requires careful optimization to operate efficiently and screen 100-300,000 compounds in a 2-6 month period. Hence a modern HTS operation is a multidisciplinary field involving analytical chemistry, biology, biochemistry, synthesis chemistry, molecular biology, automation engineering and computer science (Fernandes, J. Biomol. Screening, 2:1 (1997)).

Any HTS instrumentations and detecting technologies, for example, radiochemical methods, non-isotopic detection methods including colorimetry, luminescence, time-resolved fluorescence, fluorescence polarization, fluorescence correlation spectroscopy, and miniaturized HTS systems (described in U.S. Pat. No. 6,610,504), may be used.

5. Kits for Assaying Inhibitors of SAH Hydrolase

The invention also provides a kit for assaying for an inhibitor of a SAH hydrolase, said kit comprises (i) SAH, (ii) a tracer, wherein the tracer is a labeled SAH or a labeled SAH analog and is not hydrolyzed by the SAH hydrolase, and (iii) a SAH hydrolase, wherein the tracer generates a detectable signal after binding to the SAH hydrolase or the SAH hydrolase is immobilized on a suitable surface. In some embodiments, said kit further comprises a mutant SAH hydrolase, wherein the mutant SAH hydrolase has binding affinity for SAH and adenosine but has attenuated catalytic activity; and wherein the tracer generates a detectable signal after binding to the SAH hydrolase and the mutant SAH hydrolase, or the SAH hydrolase and the mutant SAH hydrolase are immobilized on a suitable surface.

The kits of the invention may be in any suitable packaging. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays described herein.

C. Methods and Kits for Assaying Inhibitors of SAM-Dependent Methyltransferase

The methods described above for assaying inhibitors of SAH hydrolase may be used in combination with enzymatic reaction catalyzed by SAM-dependent methyltransferase for assaying inhibitors of SAM-dependent methyltransferase.

The invention provides a method for assaying for an inhibitor of a S-adenosylmethionine (SAM)-dependent methyltransferase, comprising: a) contacting a SAM-dependent methyltransferase with (i) a substrate of the methyltransferase, (ii) SAM, and (iii) in the presence or absence of a compound suspected of being an inhibitor of the methyltransferase, under a condition that a methyl group is transferred from SAM to the substrate and SAM is converted to SAH; b) contacting the resulting SAH with a SAH hydrolase and a tracer under a condition that allows hydrolysis of the SAH into adenosine (Ado) and homocysteine (Hcy) catalyzed by the SAH hydrolase; wherein the tracer is a labeled SAH or a labeled SAH analog and is not hydrolyzed by the SAH hydrolase; and wherein i) the tracer generates a detectable signal after binding to the SAH hydrolase, or ii) the SAH hydrolase is immobilized on a suitable surface; c) detecting binding of the tracer to the SAH hydrolase; and d) comparing the amount of binding of the tracer to the SAH hydrolase in the presence of the compound to the amount of binding in the absence of the compound, whereby an increase in the amount of binding in the presence of the compound compared to the amount of binding in the absence of the compound indicates that the compound is an inhibitor of the SAM-dependent methyltransferase.

In some embodiments, the resulting SAH is contacted with the SAH hydrolase, a mutant SAH hydrolase, and the tracer; wherein the mutant SAH hydrolase has binding affinity for SAH and adenosine but has attenuated catalytic activity; wherein i) the tracer generates a detectable signal after binding to the SAH hydrolase and the mutant SAH hydrolase, or ii) the SAH hydrolase and the mutant SAH hydrolase are immobilized on a suitable surface; and wherein the binding detected in step c) is binding of the tracer to the SAH hydrolase and the mutant SAH hydrolase.

1. SAM-Dependent Methyltransferase

Inhibitors of any SAM-dependent methyltransferase can be assayed by the methods provided herein. A variety of SAM-dependent methyltransferases are known (see generally Kagan and Clarke, Arch. Biochem. Biophys., 310(2): 417-427 (1994); and Webb, Enzyme Nomenclature, Academic Press, San Diego (1992)).

Protein-Methyltransferases

In a specific embodiment, the SAM-dependent methyltransferase to be assayed is a protein methyltransferase. Protein methyltransferases include, but are not limited to, a protein carboxylmethyltransferase (Syed et al., Biochemistry, 32(9):2242-7 (1993)) or a protein (arginine) N-methyltransferase (Casellas and Jeanteur, Biochim. Biophys. Acta, 519(1):243-54 (1978); and Casellas and Jeanteur, Biochim. Biophys. Acta, 519(1):255-68 (1978)), such as an isoaspartyl O-methyltransferase, a Γ-glutamyl O-methyltransferase and an isoprenylcysteine O-methyltransferase.

Nucleic Acid Methyltransferases

SAM-dependent methyltransferases that can be assayed include nucleic acid methyltransferases, including but are not limited to, a DNA methyltransferase, such as a DNA $m^5C$ methyltransferase or a DNA m 6A methyltransferase (Posfai et al., Nucleic Acids Res., 17:2421-2435 (1989); and Lauster et al., J. Mol. Biol., 206:313-321 (1989)), which preferably include an amino acid consensus sequence of hh(D/S)(L/P)FXGXG (Lauster et al., J. Mol. Biol., 206:313-321 (1989)), where h is a hydrophobic amino acid residue (Wu et al., J. Gen. Microbiol., 138:2101-2112 (1992)).

Further examples of SAM-dependent DNA methyltransferases that can be assayed include, but are not limited to, Pvull DNA (cytosine-N4)-methyltransferase (Adams and Blumenthal, Biochemistry 36(27):8284-92 (1997)), Kpnl DNA methyltransferase (Finta et al., Gene 164(1):65-9 (1995)), EcoKl methyltransferase (Powell et al., Nucleic Acids Res., 23(6):967-74 (1995)), EcoP15 DNA methyltransferase (Ahmad and Rao, Gene, 142(1):67-71 (1994)), EcoK methyltransferase (Powell et al., J. Mol. Biol., 234 (1):60-71 (1993)), phage T4 Dam DNA-[N6-adenine]-methyltransferase (Kossykh et al., Nucleic Acids Res., 21(20): 4659-62 (1993)), Dam methyltransferase from *Escherichia coli* (Wenzel and Guschlbauer, Nucleic Acids Res., 21(19): 4604-9 (1993)), HhaI DNA methyltransferase (Cheng et al., Cell, 74(2):299-307 (1993); and O'Gara et al., J. Mol. Biol., 287(2):201-9 (1999)), and EcoRII methyltransferase (Som and Friedman, J. Biol. Chem., 266(5):2937-45 (1991)).

Also contemplated are RNA methyltransferases, including, but not limited to, mRNA, a rRNA and tRNA methyltransferases, such as the vaccinia virus mRNA (guanine-7-)methyltransferase (Higman and Niles, J. Biol. Chem., 269(21):14982-7 (1994)), which include, for example, rRNA G methyltransferase, a rRNA N6 A methyltransferase and a rRNA N6,N6 A methyltransferase. The tRNA methyltransferase include, tRNA C5 U methyltransferase, tRNA N1 G methyltransferase and tRNA N2,N2 G methyltransferase.

Lipid Methyltransferases

Lipid methyltransferases include, but are not limited to, DHPB O-methyltransferase, DHHB O-methyltransferase, UbiG O-methyltransferase, phosphatidylethanolamine methyltransferase (Zawad and Sulser, Eur. J. Biochem., 124(1-2):157-60 (1986)), phospholipid methyltransferase, cyclopropane fatty acid synthase, delta 24-sterol-C-methyltransferase (Shi et al., J. Biol. Chem., 271(16):9384-9 (1996)), and delta 24(25)-sterol methyltransferase (Janssen and Nes, J. Biol. Chem., 267(36):25856-63 (1992)).

Polysaccharide Methyltransferases

Polysaccharide methyltransferases that can be assayed by the methods herein include, but are not limited to, a NodS, which is an SAM-dependent methyltransferase that methylates chitooligosaccharides deacetylated at the non-reducing end (Geelen et al., Mol. Microbiol., 17(2):387-97 (1995)).

Small Molecule Methyltransferases

Small molecule methyltransferase that can be assayed include, but are not limited to, small molecule O-methyltransferases, small molecule N-methyltransferases, a small molecule S-methyltransferases and porphyrin precursor C-methyltransferases. These include an N-acetylserotonin O-methyltransferase (Itoh et al., J. Chromatogr. B. Biomed. Sci. Appl., 692(1):217-21 (1997)), a catechol O-methyltransferase (Vilbois et al., Eur. J. Biochem., 222(2):377-86 (1994); and Yu, Can. J. Biochem. Cell. Biol., 62(10):964-9 (1984)), a caffeic acid O-methyltransferase (Edwards and Dixon, Arch. Biochem. Biophys., 287(2):372-9 (1991); and Poeydomenge et al., Plant Cell Physiol., 105(2):749-50 (1994)), a caffeoyl-coenzyme A O-methyltransferase (Pakusch et al., Arch. Biochem. Biophys., 271(2):488-94 (1989)), an O-demethyl puromycin O-methyltransferase, a hydroxyneurosporene O-methyltransferase, a myo-inositol O-methyltransferase, a carminomycin O-methyltransferase, a tetracenomycin 3-O-methyltransferase, a tetracenomycin 8-O-methyltransferase, a midamycin O-methyltransferase, or an erythromycin biosynthesis O-methyltransferase.

Others include small molecule N-methyltransferases, such as a phenylethanolamine N-methyltransferase, a glycine N-methyltransferase, a guanidinoacetate N-methyltransferase (Takata and Fujioka, Biochemistry, 31 (17): 4369-74 (1992)), a histamine N-methyltransferase, or a diphthamide N-methyltransferase.

Small molecule S-methyltransferases include a thioether S-methyltransferase (Mozier et al., J. Biol. Chem., 263(10): 4527-31 (1988)), a thiopurine methyltransferase (VanLoon et al., Biochem. Pharmacol., 44(4):775-85 (1992)), or a L-methionine S-methyltransferase (Pimenta et al., Plant Physiol., 118(2):431-8 (1998); and James et al., J. Biol. Chem., 270(38):22344-50 (1995)).

Other examples include, porphyrin precursor C-methyltransferase, such as a magnesium protoporphyrin IX methyltransferase (Hinchigeri et al., FEBS Lett., 407(3):337-42 (1997); Gibson et al., FEBS Lett., 352(2):127-30 (1994); and Bollivar et al., J. Bacteriol., 176(17):5290-6 (1994)); an uroporphyrinogen III methyltransferase (Leustek et al., J. Biol. Chem., 272(5):2744-52 (1997); De Mot et al., Gene, 150(1):199-200 (1994); Robin et al., J. Bacteriol., 173(15): 4893-6 (1991); and Blanche et al., J. Bacteriol., 173(15): 4637-45 (1991)), a precorrin-2 methyltransferase (Thibaut et al., J. Bacteriol., 172(11):6245-51 (1990)) or a precorrin-3 methyltransferase.

Further examples of small molecule methyltransferases that can be assayed include a salicylic acid carboxylmethyltransferase (Ross et al., Arch. Biochem. Biophys., 367(1): 9-16 (1999)), a sialate-8-O-methyltransferase (Kelm et al., Eur. J. Biochem., 251(3):874-84 (1998)), an isoeugenol O-methyltransferase (Wang et al., Arch Biochem. Biophys., 349(1):153-60 (1998); and Wang et al., Plant Physiol., 114(1):213-21 (1997)), a scoulerine-9-O-methyltransferase (Takeshita et al., Plant Cell Physiol., 36(1):29-36 (1995)), a norcoclaurine 6-O-methyltransferase (Sato et al., Eur. J. Biochem., 225(1):125-31 (1994)), an isoliquiritigenin 2'-O-methyltransferase (Maxwell et al., Arch. Biochem. Biophys., 293(1):158-66 (1992)), a N-acylneuraminate 8-O-methyltransferase (Bergwerff et al., Biochimie., 74(1):25-37 (1992)), a nucleolar 2'-O-methyltransferase (Segal and Eichler, Arch. Biochem. Biophys., 275(2):334-43 (1989)), a macrocin O-methyltransferase (Bauer et al., J. Biol. Chem., 263(30):15619-25 (1988)), a 3-methylquercetin 7-O-methyltransferase (Khouri et al., Arch. Biochem. Biophys., 265 (1):1-7 (1988)), a nicotinic acid-N-methyltransferase (Upmeier et al., Arch. Biochem. Biophys., 262(2):445-54 (1988)), an avitexin 2"-O-rhamnoside 7-O-methyltransferase (Knogge and Weissenbock, Eur. J. Biochem., 140(1): 113-8 (1984)), a demethylmycophenolic acid O-methyltransferase (Muth and Nash, Antimicrob. Agents Chemother., 8(3):321-7 (1975)), a cycloartenol methyltransferase (Wojciechowski et al., Biochem. J., 136(2):405-12 (1973)) and a loganic acid methyltransferase (Madyastha et al., J. Biol. Chem., 248(7):2497-501 (1973)).

In a specific embodiment, the SAM-dependent methyltransferase to be assayed include at least one of the following amino acid consensus sequences (see generally Kagan and Clarke, Arch. Biochem. Biophys., 310(2):417-427 (1994)):

motif I ((V/I/L)(L/V)(D/E)(V/I)G(G/C)G(T/P)G) (SEQ ID NO:3);

motif II ((P/G)(Q/T),(F/Y/A)DA(I/V/Y)(F/I)(C/V/L)) (SEQ ID NO:4); and motif III (LL(R/K)PGG(R/I/L)(L/I)(L/F/I/V)(I/L)) (SEQ ID NO:5).

In another embodiment, the SAM-dependent methyltransferase includes all the motifs I, II and III in the order of N'-I-II-III-C', the distance between the last amino acid residue of motif I and the first amino acid residue of motif II is from about 36 to about 90 amino acid residues, and the distance between the last amino acid residue of motif II and the first amino acid residue of motif III is from about 12 to about 38 amino acid residues.

In another embodiment, the SAM-dependent methyltransferase only includes the motif I. In another preferred embodiment, the SAM-dependent methyltransferase includes only the motifs I and III.

In another embodiment, the SAM-dependent methyltransferase is that having the amino acid sequence set forth in SEQ ID No. 2 of U.S. Pat. No. 6,610,504 or conservative variant thereof, and that is encoded by the sequence of nucleotides set forth in SEQ ID No. 1 of U.S. Pat. No. 6,610,504 or degenerate variants thereof (see, also, U.S. Pat. No. 5,876,996 (SEQ ID NOs:1-2)).

Other SAM-dependent methyltransferases are also described in U.S. Pat. No. 6,610,504 (See e.g., TABLE 2). Other examples of SAM-dependent methyltransferases are SAM-dependent homocysteine S-methyltransferase, DNA-(cytosine-5)-methyltransferase, AIRE, DNA methyltransferase 1, DNMT1, tRNA methyltransferase, ARHI, isoprenylcysteine carboxymethyltransferase (Icmt), DNA methyltransferases 3A and 3B, histone methyltransferases, P16, MLH1, and O(6)-methylguanine-DNA methyltransferase (MGMT), HRK methyltransferase, GSTP1 CpG island DNA methyltransferase, phenylethanolamine-N-methyltransferase (PNMT), phosphatidylethanolamine N-methyltransferase (PEMT).

2. Kits for Assaying Inhibitors of SAM-Dependent Methyltransferase

The invention also provides a kit for assaying for an inhibitor for S-adenosylmethionine (SAM)-dependent methyltransferase, comprising a SAM-dependent methyltransferase, a SAH hydrolase, and a tracer; wherein the tracer is a labeled SAH or a labeled SAH analog and is not hydrolyzed by the SAH hydrolase; and wherein i) the tracer generates a detectable signal after binding to the SAH hydrolase, or ii) the SAH hydrolase is immobilized on a suitable surface. In some embodiments, the kit further comprises a mutant SAH hydrolase, wherein the mutant SAH hydrolase has binding affinity for SAH and adenosine but has attenuated catalytic activity; and wherein the tracer generates a detectable signal after binding to the SAH hydrolase and the mutant SAH hydrolase, or the SAH hydrolase and the mutant SAH hydrolase are immobilized on a suitable surface.

The kits of the invention may be in any suitable packaging. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays described herein.

D. EXAMPLES

The following examples are included for illustrative purposes only and are not intended to limit the scope of the invention.

Example 1

Assay for Inhibitors of SAH Hydrolase

The screening was carried out on a 384-balck plate, and each assay mixture was in a total of 60 µl volume. Each assay mixture containing 400 nM SAH hydrolase, 200 nM mutant SAH hydrolase, 100 nM SAH, and 40 nM rhodamine-labeled SAH in 50 mM Tris HCl (pH 8.0) was incubated with 20 µl of screening sample (from a chemical library) at room temperature for 30 min. Fluorescence polarization was determined on Perkin-Elmer Life Sciences Victor V multilabel plate reader. Adenosine (100 nM) was used as the negative control.

Using the assay described above, a group of non-nucleoside components that have $K_i$ values ranging from 8-200 nM against human SAH hydrolase was identified.

Example 2

Assay for Inhibitors of SAM-Dependent Methyltransferase

The screening was carried out on a 384-balck plate, and each assay mixture was in a total of 60 µl volume. Each assay mixture containing 20 nM histone methyltransferase, 400 nM SAH hydrolase, 2 µM histone methyltransferase substrate, 100 nM SAM, 200 nM mutant SAH hydrolase, and 40 nM rhodamine-labeled SAH in 50 mM Tris HCl (pH 8.0) was incubated with 20 µl of screening sample (from a chemical library) at room temperature for 30 min. Fluorescence polarization was determined on Perkin-Elmer Life Sciences Victor V multilabel plate reader. Adenosine (100 nM) was used as the negative control.

A compound with good inhibitory activity against histone methyltransferase had a florescence polarization shown in FIG. 1A, and a compound without inhibitor activity against histone methyltransferase had a florescence polarization shown in FIG. 1B.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

---

The claimed invention is:

1. A method for assaying for an inhibitor of a S-adenosylmethionine (SAM)-dependent methyltransferase, comprising:
   a) contacting a SAM-dependent methyltransferase with (i) a substrate of the methyltransferase, (ii) SAM, and (iii) in the presence or absence of a compound suspected of being an inhibitor of the methyltransferase, under a condition that a methyl group is transferred from SAM to the substrate and SAM is converted to SAH:
   b) contacting the resulting SAH with a SAH hydrolase and a tracer under a condition that allows hydrolysis of the SAH into adenosine (Ado) and homocysteine (Hcy) catalyzed by the SAH hydrolase; wherein the tracer is a labeled SAH or a labeled SAH analog and is not hydrolyzed by the SAH hydrolase; wherein the SAH hydrolase is wildtype or has one or more conservative amino acid substitutions that do not substantially alter its catalytic activity, and wherein
      i) the tracer generates a detectable signal after binding to the SAH hydrolase, or
      ii) the SAH hydrolase is immobilized on a suitable surface;
   c) detecting binding of the tracer to the SAH hydrolase; and
   d) comparing the amount of binding of the tracer to the SAH hydrolase in the presence of the compound to the amount of binding in the absence of the compound, whereby an increase in the amount of binding in the presence of the compound compared to the amount of binding in the absence of the compound indicates that the compound is an inhibitor of the SAM-dependent methyltransferase.

2. The method of claim 1, wherein the SAM-dependent methyl transferase is selected from the group consisting of a protein methyltransferase, a nucleic acid methyltransferase, a lipid methyltransferase, a polysaccharide methyltransferase and a small molecule methyltransferase.

3. The method of claim 1, wherein the substrate is selected from a group consisting of a protein, a nucleic acid, a lipid, and a small molecule, and wherein the SAM-dependent methyltransferase is selected from the group consisting of a protein methyltransferase, a nucleic acid methyltransferase, a lipid methyltransferase, and a small molecule methyltransferase.

4. The method of claim 1, wherein the label is a fluorescent.

5. The method of claim 4, wherein the binding of the tracer to SAH hydrolase is detected by detecting the fluorescent polarization of the tracer.

6. The method of claim 1, wherein a plurality of compounds suspected of being inhibitors of the SAM dependent methyltransferase are assayed simultaneously.

7. The method of claim 6, wherein the assay is conducted in a multi-well format.

8. The method of claim 6, wherein the SAH hydrolase is linked to a solid support.

9. The method of claim 8, wherein the SAH hydrolase is arranged in an array on the solid support.

* * * * *